(12) United States Patent
Chang et al.

(10) Patent No.: US 7,763,722 B2
(45) Date of Patent: Jul. 27, 2010

(54) SMALL INTERFERENCE RNA GENE THERAPY

(75) Inventors: Lung-Ji Chang, Gainesville, FL (US); Jin He, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 121 days.

(21) Appl. No.: 10/542,461

(22) PCT Filed: Jan. 15, 2004

(86) PCT No.: PCT/US2004/001320

§ 371 (c)(1),
(2), (4) Date: Aug. 8, 2006

(87) PCT Pub. No.: WO2004/065549

PCT Pub. Date: Aug. 5, 2004

(65) Prior Publication Data

US 2006/0269518 A1  Nov. 30, 2006

Related U.S. Application Data

(60) Provisional application No. 60/440,987, filed on Jan. 17, 2003.

(51) Int. Cl.
  *C07H 21/04* (2006.01)
  *C07H 21/02* (2006.01)
  *A61K 48/00* (2006.01)
  *C12N 15/63* (2006.01)
(52) U.S. Cl. .................... 536/24.5; 536/23.1; 514/44; 435/320.1
(58) Field of Classification Search ........................ None
See application file for complete search history.

(56) References Cited

U.S. PATENT DOCUMENTS

| 5,734,039 | A  | * | 3/1998 | Calabretta et al. | ......... 536/24.5 |
| 7,195,916 | B2 | * | 3/2007 | Qin et al. | ................ 435/465 |
| 2003/0157691 | A1 | | 8/2003 | Qin et al. | |
| 2003/0203868 | A1 | * | 10/2003 | Bushman et al. | ......... 514/44 |

FOREIGN PATENT DOCUMENTS

| WO | WO 02/097114 A2 | 12/2002 |
| WO | WO 03/079757 A2 | 10/2003 |

OTHER PUBLICATIONS

Qin et al., Inhibiting HIV-1 infection in human T cells by lentiviral-mediated delivery of small interfering RNA against CCR5, 2003, PNAS, vol. 100, No. 1, pp. 183-188.*
Chang et al., Lentiviral siRNAs targeting multiple highly conserved RNA sequences of human immunodeficiency virus type 1, 2005, Gene Therapy, 12, pp. 1133-1144.*
Hendrie et al., Chromosomal Integration and Homologous Gene Targeting by Replication-Incompetent Vectors Based on the Autonomous Parvovirus Minute Virus of Mice, 2003, Journal of Virology, pp. 13136-13145.*
Barton et al. "Retroviral delivery of small interfering RNA into primary cells", PNAS, (2002), vol. 99, No. 23, pp. 14943-14945.
Noda et al. "Protection from Anti-TCR/CD3-induced Apoptosis in Immature Thymocytes by a Signal Through Thymic Shared Antigen-1/Stem Cell Antigen-2", J. Exp. Med., (1996), vol. 183, pp. 2355-2360.
Treister et al. "Expression of Ly-6, A Marker for Highly Malignant Murine Tumor Cells, is Regulated by Growth Conditions and Stress", Int. J. Cancer, (1998), vol. 77, pp. 306-313.
McManus et al. "Gene Silencing in Mammals by Small Interfering RNAs", Nature Reviews/Genetics, (2002), vol. 3, pp. 737-747.
Tuschl et al. "Small Interfering RNAs: A Revolutionary Tool for the Analysis of Gene Function and Gene Therapy", Molecular Interventions, (2002), vol. 2, No. 3, pp. 158-167.
Rubinson et al. "A lentivirus-based system to functionally silence genes in primary mammalian cells, stem cells and transgenic mice by RNA interference", Nature Genetics, (2003), vol. 33, pp. 401-406.
He et al. "Functional Characterization of Hepatoma-Specific Stem Cell Antigen-2", Molecular Carcinogenesis, (2004), vol. 40, pp. 90-103.
Banerjea et al. "Inhibition of HIV-1 by Lentiviral Vector-Transduced siRNAs in T Lymphocytes Differentiated in SCID-hu Mice and CD34 Progenitor Cell-Derived Macrophages", Molecular Therapy, (2003), vol. 8, No. 1, pp. 62-71.
Lee et al. "Inhibition of Human Immunodeficiency Virus Type 1 Replication in Primary Macrophages by Using Tat- or CCR5-Specific Small Interfering RNAs Expressed from a Lentivirus Vector", Journal of Virology, (2003), vol. 77, No. 22, pp. 11964-11972.
Lee et al. "Expression of small interfering RNAs targeted against HIV-1 rev transcripts in human cells", Nature Biotechnology, (2002), vol. 19, pp. 500-505.
Novina et al. "siRNA-directed inhibition of HIV-1 infection", Nature Medicine, (2002), vol. 8, No. 7, pp. 681-686.
Coburn et al. "Potent and Specific Inhibition of Human Immunodeficiency Virus Type 1 Replication by RNA Interference", Journal of Virology, (2002), vol. 76, No. 18, pp. 9225-9231.
Boden et al. "Promoter choice affects the potency of HIV-1 specific RNA interference", Nucleic Acids Research, (2003), vol. 31, No. 17, pp. 5033-5038.
Pusch et al. "Nucleotide sequence homology requirements of HIV-1-specific short hairpin RNA", Nucleic Acids Research, (2003), vol. 31, No. 22, pp. 6444-6449.

(Continued)

*Primary Examiner*—Amy Bowman
(74) *Attorney, Agent, or Firm*—Timothy H. Van Dyke; Beusse Wolter Sanks Mora & Maire

(57) ABSTRACT

Gene expression is inhibited in a cell by introducing into the cell a lentiviral vector encoding a siRNA specific for the gene. Lentiviral vectors encoding siRNA specific for a cancer-associated gene inhibited expression of the gene and caused cell death after being introduced into cancer cells. Viral replication in HIV-infected cells was inhibited after introducing a lentiviral vector encoding siRNA specific for HIV genes in into the cells.

9 Claims, 3 Drawing Sheets

OTHER PUBLICATIONS

Chang et al. "Lentiviral siRNAs targeting multiple highly conserved RNA sequences of human immunodeficiency virus type 1", Gene Therapy, (2005), vol. 12, pp. 1133-1144.

Brummelkamp et al., Stable suppression of tumorigencity by virus-mediated RNA interference, Cancer Cell, vol. 2, pp. 243-247 (Sep. 2002).

Bennasser et al., RNai Therapy for HIV Infection, Biodrugs 2007: 21(1), pp. 17-22.

Brake et al., Lentiviral vectors that carry anti-HIV shRNAs: problems and solutions, J. of Gene Medicine, 9, pp. 743-750, May 2007.

An et al., Stable reduction of CCR5 by RNAi through hematopoietic stem cell transplant in non-human primates, PNAS, vol. 104, No. 32, pp. 13110-13115, Aug. 7, 2007.

Rossi et al., Genetic therapies against HIV, Nature Biotechnology, vol. 25, No. 12, Dec. 2007.

* cited by examiner

SMALL INTERFERENCE RNA GENE THERAPY

CROSS-REFERENCE TO RELATED APPLICATIONS

The present application claims the priority of U.S. provisional application Ser. No. 60/440,987 filed on Jan. 17, 2003.

STATEMENT AS TO FEDERALLY SPONSORED RESEARCH

The invention was made with U.S. government support under grant number P50 HL59412 awarded by the National Institutes of Health. The U.S. government may have certain rights in the invention.

FIELD OF THE INVENTION

The invention relates generally to fields of biology, oncology, and gene therapy. More particularly, the invention relates to a method of modulating gene expression using a lentiviral vector encoding small interference RNA (siRNA).

BACKGROUND

Double-stranded RNA (dsRNA)-mediated gene silencing or RNA interference (RNAi) was discovered and used as a genetic tool to "knockout" gene expression in the nematode *Caenorhabditis elegans* (P. Sharp, Genes & Development 13:139-141, 1999). This gene silencing phenomenon was later found to be highly conserved in many eukaryotic cells. Introduction of long dsRNA into the cells of organisms leads to the sequence-specific degradation of homologous gene transcripts. The long dsRNA molecules are metabolized to small (e.g., 21-23 nucleotide (nt)) interfering RNAs (siRNAs) by the action of an endogenous ribonuclease known as Dicer (Grishok et al., Science 287:2494-2497, 2000; and Zamore et al., Cell 101:25-33, 2000). The siRNA molecules bind to a protein complex, termed RNA-induced silencing complex (RISC), which contains a helicase activity and an endonuclease activity. The helicase activity unwinds the two strands of RNA molecules, allowing the antisense strand to bind to the targeted RNA molecule (Zamore et al., Cell 101:25-33, 2000; Zamore, P. D., Science 296:1265-1269, 2002; and Vickers et al., J Biol Chem. 2003 Feb. 28; 278(9):7108-18). The endonuclease activity hydrolyzes the target RNA at the site where the antisense strand is bound. Therefore, RNAi is an antisense mechanism of action, as a single stranded (ssRNA) RNA molecule binds to the target RNA molecule by Watson-Crick base pairing rules and recruits a ribonuclease that degrades the target RNA.

Another post-transcriptional gene silencing process is mediated by micro RNA, or miRNA, a ssRNA species which suppress mRNA translation (Lee et al., Cell 75, 843-54 (1993)). Like siRNA, miRNA are derived from RNA precursors that are processed to 21-25 nt sequences by endonuclease Dicer and form a sequence specific gene silencing complex. See, McManus & Sharp, Nat Rev Genet 3, 737-47. (2002).

In mammalian cells, dsRNA longer than 30 bp can cause non-specific gene suppression by an interferon α response. However, cells transfected with 21 nt synthetic double-stranded siRNA bearing two nucleotides protruding at both 3'-ends may escape an interferon response and effectively exert sequence-specific gene silencing function. The silencing effect of the synthetic siRNA, however, is transient. Plasmid DNA expressing siRNA has also been developed utilizing transcription systems including T7 polymerase, and mammalian pol II or pol III promoters. Wang et al., J Biol Chem 275, 40174-9 (2000); Yu et al., Proc Natl Acad Sci USA 99, 6047-52 (2002). The effectiveness of gene silencing by siRNA-encoding plasmids depends on DNA transfection efficiency, which can be low for many cell types and, in particular, for in vivo studies. Plasmid DNA transfection also results in transient siRNA expression. For effective gene silencing, e.g., as might be desired for a gene therapy application, a system that provides high levels of siRNA expression for prolonged periods would be desirable.

SUMMARY

The invention relates to methods and compositions for modulating gene expression in a cell using a lentiviral vector encoding an siRNA. To modulate (e.g., reduce) gene expression in a cell, a lentiviral vector encoding a siRNA specific for the gene to be modulated is introduced into the cell. Once the lentiviral vector is introduced into the cell, the siRNA molecule(s) is expressed and acts to promote degradation of complementary RNA sequences, preventing expression of the gene encoded by these sequences.

In the experiments described below, one example of a lentiviral vector encoding siRNA used to reduce expression of a particular gene in mammalian cells is described. Lentiviral vectors encoding pol III promoter-driven siRNA specific to stem cell antigen-2 (Sca-2), a tumor specific gene, efficiently silenced Sca-2 expression in a murine hepatoma cell line, and induced rapid apoptotic cell death.

A significant advantage to this system is that it can achieve stable and long-lasting expression of the siRNA. For example, in the experiments described above, Sca-2 expression was inhibited by more than 90% after lentiviral siRNA vector transduction. Moreover, this silencing effect lasted at least two months when the vector contained a reverse-oriented pol III-siRNA.

Additional experiments presented below show that lentiviral vectors encoding siRNA can be used to inhibit viral replication in cells. In particular, several lentiviral siRNA vectors targeting multiple highly conserved regions in the HIV type 1 (HIV-1) genome were developed and tested. Although vector production might have been expected to be suppressed because some of the siRNAs targeting sites were also present in the helper construct of the vector system, the production of these lentiviral siRNA vectors was not significantly affected. When tested against different HIV-1 molecular clones, siRNAs targeting gag, pol, int and vpu genes efficiently inhibited replication of all strains. These lentiviral siRNA vectors also protected host cells from syncytium-forming, macrophage-tropic HIV-1 induced cytotoxicity. And transduction of a long term chronically infected human lymphoma cell line with lentiviral siRNAs resulted in stable inhibition of HIV-1 replication.

Accordingly, the invention features a lentiviral vector (e.g., a self-inactivating vector) that includes a nucleotide sequence encoding a small interference RNA. The lentiviral vector can be one included within a lentiviral virion. The small interference RNA can be on specific for a gene associated with cancer such as Sca-2 or it can be specific for a gene present in a virus (e.g., HIV) such as gag, pol, int, or vpu from HIV-1.

The vector can include a cassette that features a promoter and the nucleotide sequence encoding the small interference RNA. The cassette can be in a reverse orientation or a forward orientation with regard to the viral vector genome.

In another aspect, the invention features a method that includes the step of introducing a lentiviral vector of the invention (e.g., one including a nucleotide sequence encoding a small interference RNA) into a cell. The cell can be a mammalian cell such as a human cell. The cell can also be a tumor cell.

In one variation of the method of the invention, the small interference RNA is specific for a gene associated with cancer such that the step of introducing the nucleic acid into the cell results in decreased expression of the gene and/or death of the cell.

In another variation of the method of the invention, the cell is infected with a virus and the small interference RNA is specific for a gene present in the virus (e.g., HIV) such as gag, pol, int, or vpu from HIV-1. In this variation, the step of introducing the vector into the cell can result in the inhibition of replication of the virus in the cell.

The vector used in the method of the invention can include a cassette that features a promoter and the nucleotide sequence encoding the small interference RNA. The cassette can be in a reverse orientation or a forward orientation relative to other genes (i.e., genes making up the viral genome) in the vector. The step of introducing the vector into the cell can result in expression of the nucleotide sequence encoding a small interference RNA for longer than three weeks.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes VII, Oxford University Press: New York, 1999. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1st edition, Springer-Verlag: New York, 2002. Commonly understood definitions of microbiology can be found in Singleton and Sainsbury, Dictionary of Microbiology and Molecular Biology, 3rd edition, John Wiley & Sons: New York, 2002.

By the term "gene" is meant a nucleic acid molecule that codes for a particular protein, or in certain cases, a functional or structural RNA molecule.

As used herein, the term "vector" refers to a nucleic acid molecule capable of transporting another nucleic acid to which it has been linked. As used herein, the term "lentiviral vector" refers to a vector derived from (i.e., sharing nucleotides sequences unique to) a lentivirus.

By "small interfering RNA" or "siRNA" is meant a RNA typically about 21-23 nucleotides long that mediates messenger RNA catalysis.

A first nucleic-acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

DETAILED DESCRIPTION

Figure 1:
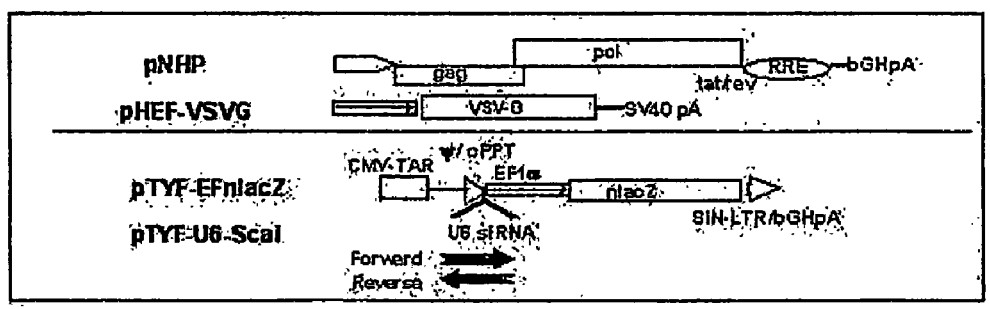
FIG. 1 is a schematic illustration of lentiviral siRNA targeting Sca-2 and long term suppression of Sca-2 expression after lentiviral transduction. (A) The lenti-siRNA vector system and viral titers. The 21-nt Sca-2 mRNA target site from nt 340 to 360 is shown, so is the predicted U6 promoter-encoded siRNA stem-loop. (B) The lenti-siRNA vector system. The siRNA expression cassette U6-Sca-2 siRNA was inserted into transducing vector pTYF-EFnlacZ between the central polypurine tract (cPPT) and the EF1α promoter in either forward or reverse orientation. Viral vector was generated by co-transfecting 293T cells with pTYF transducing plasmid, pHP and pHEF-VSVG plasmids.

The invention provides methods and compositions for modulating gene expression in a cell using a lentiviral vector encoding siRNA. In the experiments described herein, lentiviral vectors encoding siRNA are used to reduce expression of a specific gene in mammalian cells and to inhibit HIV-1 replication in cells.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc., 103:3185, 1981. Chemical synthesis of nucleic acids can be performed, for example, on commercial automated oligonucleotide synthesizers. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P.

D. Robbins, Humana Press, 1997; and Retro-vectors for Human Gene Therapy, ed. C. P. Hodgson, Springer Verlag, 1996.

Nucleic Acids and Methods of Use

The invention provides a nucleic acid that includes a lentiviral vector; and a nucleotide sequence encoding a siRNA. The nucleic acid can be used to inhibit expression of a target gene in a cell. The lentiviral vector portion of the nucleic acid provides those sequences necessary for production of virus and expression of the nucleotide sequence encoding a siRNA. The siRNA portion of the nucleic acid encodes a polynucleotide that, when expressed in a cell, can inhibit expression of a target gene by RNA interference. Any lentiviral vector and nucleotide encoding a siRNA that is suitable for a particular application of the invention might be used. Several examples are described below.

Lentiviral Vectors

A number of different type of lentiviral vectors are known including naturally occurring lentiviruses such as human immunodeficiency virus 1 (HIV-1), HIV-2, simian immunodeficiency virus (SIV), feline immunodeficiency virus (FIV), bovine immunodeficiency virus (BIV) and others. See U.S. Pat. No. 6,207,455. Because of the many advantages HIV-1 based vectors provide for gene therapy applications, these are presently preferred, although other vectors derived from other lentiviruses might also be used by adapting the information described herein.

To render HIV-1 derived vectors safe and efficient for gene therapy application, it is desirable to (1) delete the maximum amount of the virus sequence that avoids the production of wild type virus by recombination without interfering with the virus efficacy and (2) insert heterologous sequences to increase the efficacy of the vector. An example of such a vector has been made starting from HIV-1 proviral DNA. For example, because efficient synthesis of HIV-1 Gag-Pol requires tat activation of the LTR and the interaction of Rev-RRE to mediate nuclear export of mRNA, these functions should be retained. On the other hand, because the accessory gene functions of vif, vpr, vpu and nef have been shown to be dispensable for viral replication, one or more of these might be deleted.

The lentiviral vectors of the invention might also be pseudotyped, e.g., to overcome restricted host cell tropism. For example, lentiviral vectors pseudotyped with vesicular stomatitis virus G (VSV-G) viral envelopes might be used. In addition, the potential risk of wild type recombination can be reduced by designing a three-plasmid co-transfection strategy for vector production. Such a three-plasmid design includes a helper construct, pHP, that encodes the gag-pol (necessary viral proteins), a transducing vector construct, pTYF-nlacZ, that encodes a siRNA and the viral genome which carries a foreign gene cassette (reporter gene), and a VSV-G envelope expression plasmid (e.g., pHEF-VSVG). To increase vector titer in the system, an additional eukaryotic expression plasmid (e.g., a transactivator plasmid construct such as pCEP4-tat) might also be utilized.

To enhance safety, a SIN lentiviral vector might also be used. For example, a SIN lentiviral vector can be made by inactivating the 3' U3 promoter and deleting of all the 3' U3 sequence except the 5' integration attachment site which is important for the integration into a host chromosome. A particularly preferred construct for designing vectors of the invention is pTYF-nlacZ shown in FIG. 1.

siRNA Specific for Target Genes

The lentiviral siRNA vectors of the invention may be used to modulate expression of (e.g., silence or suppress) any suitable gene (i.e., a target gene) in a cell. Modulation of gene expression in a cell can be assessed by detecting a decrease in transcription or translation of the gene or by detecting a decrease in the level or activity of an expression product (e.g., a polypeptide) of the gene, as compared to a control not with the lentiviral siRNA vector.

In some the experiments described herein, a lentiviral vector was used that encodes a siRNA specific for the Sca-2 gene. In other experiments described herein, a lentiviral vector was used that encodes a siRNA specific for HIV-1 genes. Other genes, however, may be targeted for modulation (e.g., suppression or silencing) using lentiviral siRNA vectors. Genes to be targeted using lentiviral siRNA vectors include, without limitation, those whose expression is correlated with an undesired phenotypic trait. Thus, genes relating to cancer, rheumatoid arthritis and viruses might be targeted. Cancer-related genes include oncogenes (e.g., K-ras, c-myc, bcr/abl, c-myb, c-fms, c-fos and cerb-B), growth factor genes (e.g., genes encoding epidermal growth factor and its receptor, fibroblast growth factor-binding protein), matrix metalloproteinase genes (e.g., the gene encoding MMP-9), adhesion-molecule genes (e.g., the gene encoding VLA-6 integrin), tumor suppressor genes (e.g., bcl-2 and bcl-X1), angiogenesis genes, and metastatic genes. Rheumatoid arthritis-related genes include, for example, genes encoding stromelysin and tumor necrosis factor. Viral genes include human papilloma virus genes (related, for example, to cervical cancer), hepatitis B and C genes, and cytomegalovirus (CMV) genes (related, for example, to retinitis). Numerous other genes relating to these diseases or others might also be targeted.

Control Elements

Lentiviral vectors within the invention can be made to contain various control elements such as a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Endogenous lentiviral promoters can be utilized in many applications, although the use of heterologous promoters is often preferred to increase expression of the inserted exogenous nucleic acid. Any heterologous promoter compatible with the particular lentiviral vector to be used can be employed. Examples of such heterologous promoters include the SV40 early promoter, the mouse mammary tumor virus LTR promoter, the murine leukemia virus LTR (MULV LTR), the adenovirus major late promoter (Ad MLP), adenovirus inverted terminal repeats (ITR), a herpes simplex virus (HSV) promoter, a promoter such as the CMV immediate early promoter region (CMVIE), a Rous sarcoma virus (RSV) promoter, synthetic promoters, hybrid promoters, other pol II and pol III and viral promoters, and the like. In addition, sequences derived from nonviral genes, such as the murine metallothionein gene or the metallothionein II promoter, might also be used. Many such promoter sequences are commercially available from, e.g., Stratagene (San Diego, Calif.). Other control elements that might be used include those derived from the native control elements that regulate transcription of genes encoding beta-actin, alpha-fetoprotein, gamma or beta-globulin, IL-2, and beta-interferon. Still other control elements that might be used include the elongation factor 1 (EF1) promoter, the neuron specific promoter, and the CMV enhancer beta actin hybrid promoter.

Where it is desired to be able to regulate expression of the exogenous nucleic acid, inducible control elements may be used. As an example, the tetracycline-inducible expression system (Baron and Bujard Methods Enzymol. 327:401-421, 2000; Schonig et al., NAR 30:e134, 2002; and Lamartina et al., Hum. Gene Ther. 13:199-210, 2002) could be used. Inducible lentiviral siRNA vectors containing a chimeric tetracycline-responsive element and pol III promoter are particularly useful.

Control elements such as a promoter may be operably linked to a nucleic acid encoding a siRNA to form a cassette that may be inserted into a lentiviral vector. Such a cassette may be inserted in a lentiviral vector in a forward (same direction as the lentiviral sequences) or reverse (opposite direction as the lentiviral sequences) orientation. For long-term expression of the siRNA, the reverse orientation is preferred. See Example 1 below.

Permissive Host Cells

Any cell or cell line that can be transduced with a lentiviral vector particle can be used in the invention. Examples of such cells include: Jurkat cells (a human T cell line), H9 cells (human T-lymphoid cell line), A3.01 cells (human T-lymphoid cell line), C8166 cells (human T-lymphoid cell line), COS-7 cells (an African green monkey fibroblast cell line), human peripheral blood lymphocytes (PBLs), monkey PBLs, feline PBLs, a feline CD4+ T cell line, 293 cells (a human kidney fibroblast cell line), 293T cells (a human kidney fibroblast cell line), mammalian peripheral blood dendritic cells, mammalian hepatocytes, human mast cell progenitors, mammalian macrophages, mammalian follicular dendritic cells, mammalian epidermal Langerhans cells, mammalian megakaryocytes, mammalian microglia, mammalian astrocytes, mammalian oligodendroglia, mammalian CD8+ cells, mammalian retinal cells, mammalian renal epithelial cells, mammalian cervical cells, mammalian rectal mucosa cells, mammalian trophoblastic cells, mammalian cardiac myocytes, human neuroblastoma cells, mammalian CD4+ cells, mammalian hematopoietic stem cells, mammalian glial cells, adult mammalian neural stem cells, mammalian neurons, mammalian lymphocytes, and mammalian fibroblasts. Lists of CD4+ and CD4- cell types which are infectable by HIV have been compiled (see, Rosenburg and Fauci, Adv. Immunol. 47:377-431, 1989; and Connor and Ho, 1992, in AIDS: etiology, diagnosis, treatment, and prevention, 3rd edition, Hellman and Rosenburg (eds) Lippincoft, Philadelphia Also see Vigna and Naldini, J. Gene Med. 5:308-316, 2000.

Pseudotyped lentiviral vectors may also be used in compositions and methods of the invention. For example, HIV vectors pseudotyped by transducing packaging cell lines used to package the vector with a nucleic acid which encodes the VSV envelope glycoprotein protein, which is expressed on the surface of the HIV particle. VSV infects both dividing and non-dividing CD34+ cells, and pseudotyped vectors expressing VSV envelope proteins are competent to transduce these cells. See, Naldini et al., Science 272:263, 1996; and Akkina et al., J. Virol. 70:2581, 1996.

Other cells can be checked for permissiveness by adding lentiviral vector particles to the cells (e.g., in culture or in situ) and later examining if one or more genes within the vector particles are expressed.

Administering Vectors To Cells in Culture

Lentiviral vector particles can be administered to cells in culture by transduction. For example, cell lines can be transduced with a lentiviral vector either with or without centrifugation. Vector concentrations used in the experiments described below ranged from a multiplicity of infection (MOI) of 10-20. To produce virus, cells permissive to lentiviral vector transduction (e.g., 293T cells) are transfected with the lentiviral transducing plasmid (e.g., 0.8 ug of pTYF transducing plasmid per well in a 6-well plate), a helper plasmid providing gag and pol gene products (e.g., 1.8 ug of pNHP per well in a 6-well plate), a helper plasmid encoding envelope proteins (e.g., 0.5 ug of pHEF-VSVG per well in a 6-well plate), optionally a plasmid encoding a transactivator protein (e.g., 0.2 ug of pCEP4tat per well in a 6-well plate), as well as a control plasmid (e.g., 0.2 ug of pHEFeGFP per well in a 6 well plate). Cells can be transfected with these plasmids using any suitable cell transfection technique (e.g., using Superfect, Qiagen). Subsequent to the transfection, the cells are washed and fed. Virus is then collected and pooled. In the experiments described herein, the cells were washed and fed 5 hr later, and virus was collected and pooled together at 24, 36 and 48 hr after transfection and then concentrated and titered before use. Additional protocols for the preparation and use of lentiviral vectors are described in Chang and Zaiss, Methods Mol. Med. 69:303-318, 2002.

Administering Vectors to a Host Animal

The lentiviral vector particles of the present invention can be used in a method for modulating gene expression in a host animal. In this method, a lentiviral vector encoding a siRNA specific for the gene to be modulated (e.g., suppressed) is administered to an animal in a manner in which the siRNA becomes expressed. Administration of lentiviral vectors to a host animal can be achieved by two general methods. In the first method, cells not contained within an animal (e.g., cells isolated from a mammalian subject such as PBLs; hematopoietic cells from bone marrow, fetal liver or placenta; purified hematopoietic stem cells such as CD34+ cells) are transduced with lentiviral vector particles in vitro, and the cells are then introduced into the animal (e.g., transduced isolated cells are re-infused into the animal's bloodstream). In the second method, a lentiviral vector particle is directly introduced into the animal, e.g., by intravenous injection, intraperitoneal injection, or in situ injection into target tissue. Transduced cells or lentiviral vector particles can be introduced into an animal by any suitable method. For example, a conventional syringe and needle can be used to inject a lentiviral vector particle suspension or transduced cell suspension into an animal. Depending on the desired route of administration, injection can be in situ (i.e., to a particular tissue or location on a tissue), intramuscular, intravenous, intraperitoneal, or by another parenteral route.

Parenteral administration of vectors or vector particles by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the vectors or vector particles may be in powder form (e.g., lyophilized) for constitution with a suitable vehicle, for example, sterile pyrogen-free water, before use.

Lentiviral vector or vector particles can also be delivered to an animal by inhalation by any presently known suitable technique. For example, the vectors or vector particles of the invention can be delivered in the form of an aerosol spray produced from pressurized packs or a nebulizer, with the use of a suitable propellant such as dichlorodifluromethane, trichlorotrifluoromethane, dichlorotetraflurorethane, carbon dioxide, or any other suitable gas. In the case of a pressurized aerosol, the dosage unit may be controlled using a valve to deliver a metered amount. Capsules and cartridges (e.g., of gelatin) containing a powder mix of the vector or vector particles and a suitable base (e.g., lactose or starch) can be used in an inhaler or insufflator to deliver the vector or vector particles to the respiratory tract of an animal.

Still other routes of administration might be used in the invention in certain applications. For example, the vectors or vector particles might be formulated for oral, buccal, urethral, vaginal, or rectal administration.

To facilitate delivery of the vectors or vector particles to an animal, the vectors or vector particles of the invention can be mixed with a carrier or excipient. Carriers and excipients that might used include saline (especially sterilized, pyrogen-free saline) saline buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly preferred for delivery of vectors or vector particles to human subjects. Methods for making such formulations are well known and can be found in, for example, Remington's Pharmaceutical Sciences In addition to the formulations described previously, the vectors or vector particles can also be formulated as a depot preparation. Such long acting formulations may be administered by implantation (for example subcutaneously or intramuscularly) or by intramuscular injection. Thus, for example, the vectors or vector particles may be formulated with suitable polymeric or hydrophobic materials (for example as an emulsion in an acceptable oil) or ion exchange resins, or as sparingly soluble derivatives.

Dosing

Toxicity and therapeutic efficacy of the lentiviral vectors utilized in the invention for gene therapy can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Vectors that exhibit large therapeutic indices are preferred. While those that exhibit toxic side effects may be used, care should be taken to design a delivery system that targets such vectors to the site of affected tissue in order to minimize potential damage to uninfected cells and, thereby, reduce side effects.

The data obtained from cell culture assays and animal studies can be used in formulating a range of dosage for use in humans. The dosage of such vectors lies preferably within a range of circulating concentrations that include an $ED_{50}$ with little or no toxicity. The dosage may vary within this range depending upon the dosage form employed and the route of administration utilized. For any vector used in the method of the invention, the therapeutically effective dose can be estimated initially from cell culture assays. A dose can be formulated in animal models to achieve an $IC_{50}$ (that is, the vector dose which achieves a half-maximal inhibition of symptoms) as determined in cell culture. Such information can be used to more accurately determine useful doses in humans.

Assessing Gene Silencing

Transfer of an exogenous nucleic acid into a host cell or organism by a lentiviral vector can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods. For instance, mRNA produced from an exogenous nucleic acid can be detected and quantified using a Northern blot and reverse transcription PCR (RT-PCR).

Expression of an RNA from the exogenous nucleic acid can also be detected by measuring an enzymatic activity or a reporter protein activity. For example, siRNA activity can be measured indirectly as a decrease in target nucleic acid expression as an indication that the exogenous nucleic acid is producing the effector RNA.

EXAMPLES

Example 1

Inhibition of SCA-2

Lentiviral siRNA successfully suppressed >90% of Sca-2 expression and the suppression lasted longer than three months.

Materials and Methods

Plasmid construction. The murine U6 snRNA promoter was PCR amplified from genomic DNA isolated from the murine 1MEA7R hepatoma. The PCR product was cloned into pBSKSII between EcoR I and Hind III sites to generate pBS-U6. The Sca-2 siRNA coding sequence was constructed by annealing the following two primers: sense 5'-TTT GCT CCT TCT GCA ACT TCA GTT CAA GAG ACT GAA GTT GCA GAA GGA GCT TTT TT-3' (SEQ ID NO:1) and antisense 5'-AGC TAA AAA AGC TCC TTC TGC AAC TTC AGT CTC TTG AAC TGA AGT TGC AGA AGG AG-3' (SEQ ID NO:2) and the GFP siRNA coding sequence was constructed by annealing the following two primers: sense 5'-TTT GAG AGA CCA CAT GGT CCT GTT CAA GAG ACA GGA CCA TGT GGT CTC TCT TTT T-3' (SEQ ID NO:3) and antisense 5'-AGC TAA AAA GAG AGA CCA CAT GGT CCT GTC TCT TGA ACA GGA CCA TGT GGT CTC T-3' (SEQ ID NO:4) and cloned into Bbs I and Hind III sites in pBS-U6 to generate pBS-U6siRNA constructs. To facilitate lentiviral siRNA vector construction, two different Sfi I cloning sites (A and B) were inserted upstream and downstream of the U6-siRNA region by site-specific mutagenesis and PCR, and a lentiviral SIN vector (pTYF-EFnlacZ) containing two Sfi I (A/B) sites and a 1100 bp stuffer was constructed (pTYF-Sfi A/B or B/A) for later U6-siRNA cloning. To generate lentiviral siRNA vectors, the U6-siRNA fragment was released from pBS-U6siRNA by Sfi I digestion and inserted into pTYF-Sfi A/B or pTYF-Sfi B/A to obtain either forward or reverse siRNA insertion clone. Wild type Sca-2 amino acid synonymous mutant Mu-Sca-2 was generated using PCR-based site-specific mutagenesis using the following primers: primer 1,5'-AAT CTA GAC CAC CAT GTC TGC CAC TTC CAA CAT GAG-3' (SEQ ID NO:5), primer 2,5'-GTG AAC AGC TAC TGC TGC CAA TCG TCG TTC TGC AAC TTC AGC GCA GCT G-3' (SEQ ID NO:6) and primer 3,5'-AAG AAT TCT GGT CAG GGG CTC AGC TGC AG-3' (SEQ ID NO:7) and the amplified DNA was cloned into pTYF-EFnlacZ between Spe I and EcoR I sites.

Lentiviral vector production, concentration and titration. Lentiviral vectors were generated by DNA co-transfection and the virus was concentrated by microfuge centrifigation or filtration as previously described. Chang and Zaiss. Methods for the preparation and use of lentivirus vectors. In: Morgan J, editor. Gene Therapy Protocols. 2nd ed. Volume 2, Methods in Molecular Medicine. Totowa: Humana Press, Inc.; 2001. p 303-318. The virus titer was determined on TE671 cells using β-galactosidase enzyme assay.

Cell culture, RNA transfection and virus transduction. IMEA7R and BLN.CL2 were obtained from ATCC (Manassas, Va.) and maintained in Dulbecco's modified Eagle's Medium (DMEM, Gibco BRL) containing 10% FBS and 100 units/ml of penicillin-streptomycin (Gibco BRL). The 293T and TE671 cells were cultured in DMEM with 10% FBS and propagated for a long term to establish more adherent phenotype as previously described. Id. The Sca-2 siRNA duplex oligos, sense 5'-GCT CCT TCT GCA ACT TCA GTT-3' (SEQ ID NO:8) and antisense: 5'-CTG AAG TTG CAG AAG GAG CTT-3' (SEQ ID NO:9), were chemically synthesized by Dharmacon Research, Inc. The synthetic double-stranded RNA oligos were transfected into the murine cells using oligofectamine (Dharmacon Research, Inc.) according to the manufacturer's instruction. For lentiviral transduction, $1 \times 10^5$ murine cells were transduced with different lenti-U6-siRNA viral vectors at a MOI of 10-20 in the presence of polybrene (8 ug/ml, Sigma). Transduction efficiency was monitored by reporter gene nlacZ assay as previously described. Id.

Cell division and proliferation assay. After lentiviral transduction, the tumor cells were trypsinized and suspended in 2 ml DMEM. A sample of 100 ul of cells were taken and stained with trypan blue to determine cell viability and total number. The rest were plated back for continued culture. Cell counting was carried out everyday for 7 days after transduction. The relative rates of cell division were assessed by carboxyfluorescein diacetate succinidyl ester staining (CFSE, Sigma). For CFSE, tumor cells were incubated with 5 uM CFSE in DMEM at room temperature for 10 min, after which excess CSFE was removed by washing 3 times with medium. Cells were then cultured in complete DMEM and CFSE intensity was measured by FACSCalibur over 3-day time course.

Flow cytometry. For surface protein analysis, the cells were incubated with fluorescein-conjugated Rat-anti-mouse Sca-2 monoclonal antibody (BD Biosciences), or phycoerythrin-conjugated hamster-anti-mouse TNF-α receptor 1 (Santa Cruz Biotechnology) and analyzed using FACSCalibur and the CELLQUEST program (BD Biosciences).

Northern, Southern and Western analyses. The polyA+ RNA or total RNA and genomic DNA were harvested and separated on agarose gels for Southern and Northern analyses. Total proteins were harvested and separated by 12% NuPAGE bis-Tris gel electrophoresis (Invitrogen) and transferred to nitrocellulose membrane (Schleicher & Schuell) for Western analysis. The protein blots were incubated with rabbit polyclonal anti-caspase 8 antibody (1:1000) (Santa Cruz Biotechnology), Rabbit polyclonal anti-cleaved caspase 3 antibody (1:1000), Rabbit polyclonal anti-PARP antibody (1:1000) (Cell Signaling Technology), mouse monoclonal anti-TNFα-R1 antibody (1:1000), or mouse polyclonal anti-alpha tublin antibody (1:1000) (Santa Cruz Biotechnology). The signals of caspase 3, PARP were developed with horseradish-peroxidase conjugated secondary antibodies (1:2000) by enhanced chemiluminescence. The signals of caspase 8, alpha-tubulin and TNFα-R1 were developed with biotin-conjugated secondary antibodies (1:10,000) using ImmunoPure Ultra-Sensitive ABC staining kit (Pierce) according to the manufacturer's instruction.

Apoptosis induction and assays. Tumor cells were treated with TNFα at different concentrations (0-10 ng/ml) with or without cycloheximide (5 ug/ml), or treated with cisplatin (25 uM) or ultraviolet light irradiation (10 $mJ/cm^2$) to induce apoptosis. For early apoptosis analysis, the cells were stained with FITC-Annexin/Propidium Iodide using ApopNexin Apoptosis Detection kits (Serologicals Corporation) according to the instructions. Stained tumor cells were analyzed by FACSCalibur. For apoptotic cell DNA staining, tumor cells were pelleted and re-suspended in 50 ul of 3% paraformaldehyde in PBS, incubated for 10 min at room temperature, washed once with PBS, and resuspended in 100 ul of PBS containing 32 ug/ml of bis-benzimide (Hoechst 33258, Sigma). After 15 min incubation at room temperature, the cells were spread onto a microscope slide and observed under an inverted Axioskop Zeiss fluorescent microscope (Zeiss, Germany) using a fluoro lens and filter. Apoptotic cells were scored by morphological changes including chromatin condensation and nuclear membrane blebbing.

Statistical analysis. The significance of different in data analysis was performed according to the specifications of SPSS statistics program (SPSS Inc. Chicago, Ill.).

Results

Sca-2 downregulation using siRNA gene knock-down approach. Sca-2 was identified as being overexpressed in cancer cells. To investigate the role of Sca-2 in tumorigenesis, Sca-2 mRNA was targeted with a 21-nt synthetic siRNA. The murine hepatoma cells were transfected with the 21-nt siRNA, and Sca-2 protein and RNA were analyzed by FACS using specific anti-Sca-2 antibody and by Northern blotting, respectively. The siRNA effectively down-regulated Sca-2 expression 3 days after transfection as shown by FACS and by total RNA Northern blotting. The cells transfected with the 21-nt Sca-2 siRNA underwent rapid cell death within 1-2 days. This was not observed in the control transfected cells. The effects of Sca-2 suppression and tumor cell death were transient in the transfected cells, as Sca-2 expression and cell growth reverted to normal levels 10 days after transfection.

Long term suppression of Sca-2 expression after lentiviral siRNA transduction. To study the Sca-2 function and the siRNA effects in long term, lentiviral siRNA vector targeting the same site that was found effective with the synthetic siRNA were constructed FIG. 1A. A murine snU6 promoter-siRNA cassette was inserted into the lentiviral SIN vector 5' to an internal EF1α-nlacZ reporter gene in either forward or reverse orientation according to the viral genome, and lentiviral vectors were produced using helper plasmid pNBP and pVSV-G as depicted in FIG. 1B and described in previous studies. Chang and Zaiss, Methods for the preparation and use of lentivirus vectors. In: Morgan J, editor. Gene Therapy Protocols. 2nd ed. Volume 2, Methods in Molecular Medicine. Totowa: Humana Press, Inc.; 2001, p 303-318; and Zaiss et al., J Virol 2002; 76:7209-7219. Both forward (lenti-Scai-F) and reverse (lenti-Scai-R) siRNA lentiviral constructs produced similar vector titers compared to the control lenti-EFnlacZ.

The hepatoma cells were infected with either of the two lentiviral Sca-2 siRNA vectors or with a control lentiviral U6 promoter vector (lenti-U6P). Infection efficiency was monitored by lacZ reporter gene assay, and analyzed Sca-2 expression by FACS and Northern analyses at different time periods after transduction. The results showed that the hepatoma cells were efficiently infected by the lentiviral vectors (~100%), and both forward and reverse lentiviral Sca-2 siRNA vectors efficiently suppressed Sca-2 expression (~80-90%). The inhibition effect of the lentiviral siRNA vectors was stable for longer than 3 weeks. Consistent with the transient siRNA transfection result, tumor cell death was observed soon after transduction. The forward and reverse lentiviral siRNA vectors showed only marginal difference in Sca-2 suppression in the short term.

The transduced tumor cells were continuously propagated for 2 months, and then analyzed for Sca-2 expression. The lenti-Scai-R vector maintained efficient inhibitory effect (~90%), but the forward lenti-Scai-F vector gradually lost its inhibitory effect to ~50-60%, as determined by both FACS and RNA blotting. The efficiency of inhibition correlated well with transduction efficiency as observed in a nlacZ gene assay. Southern analysis revealed that the decreased inhibition correlated with decreased number of cells carrying the transgenes. Similarly constructed lentiviral siRNA vectors driven by a different pol-III promoter, the human H1 RNA promoter, cloned in both forward and reverse orientations also demonstrated high inhibitory efficiency and long term stable effects with the reverse siRNA construct.

Sca-2 suppression induced tumor cell apoptosis. To obtain a homogenous cell population, Sca-2 positive cells were sorted using anti-Sca-2 antibody by flow cytometry. The sorted Sca-2$^+$ cells were again transduced with the Sca-2 lentiviral siRNA vectors and Sca-2 expression was efficiently inhibited (>90%). The effect of Sca-2 inhibition on tumor cell growth was analyzed by counting dividing cells at different time points. Compared with control cells (lenti-U6P), the growth rate of tumor cells transduced with both forward and reverse lentiviral Sca-2 siRNA vectors (lenti-Scai F and R) decreased significantly. Cells were analyzed for apoptosis using annexin/PI staining and FACS analysis. The results showed that a significant portion of Sca-2-inhibited tumor cells underwent early apoptosis, evidenced by increased PI-negative and annexin-positive cell population (39.88%). This result was confirmed by morphological characterization of cells displaying nuclear condensation and membrane blebbing using Hoechst dye staining. Using assays including CFSE viable cell staining and cell cycle PI staining, no difference in cell cycle progression after Sca-2 suppression was detected.

Tumor cells with suppressed Sca-2 were sensitive to extrinsic but not intrinsic apoptosis signals. The lentiviral-Sca-2 siRNA transduced tumor cells gradually recovered from apoptosis after two weeks, and continued to propagate with Sca-2 suppressed. Since the inhibition of Sca-2 induced rapid apoptosis, whether the recovered cells would react differently to extrinsic and intrinsic apoptotic signals was investigated. The common death receptor-mediated apoptosis in liver cells involve TNFα/TNFα receptor (TNFR) and Fas/FasL signaling pathways. The tumor cells were treated with TNFα in the presence or absence of cycloheximide (CHX) for the analysis of extrinsic (or death receptor-mediated) apoptotic signaling. The apoptosis was determined by Hoechst dye staining and enumeration of apoptotic cells based on morphological changes at 6 h and 36 h after treatment. The results showed that the hepatoma cells responded to TNFα-induced cell death in a dosage-dependent manner, and tumor cells with suppressed Sca-2 expression (lenti-scai-R) were more sensitive to TNFα-mediated cell death than the controls. To confirm this finding, procaspase 8, caspase 3 and poly-(ADP-ribose) polymerase (PARP) were analyzed by Western analysis, all of which are key components to the TNFα receptor 1 (TNFR1)-mediated apoptosis pathway. Kinetic analyses of these proteins demonstrated that lenti-scai-R transduced hepatoma cells displayed increased rates of procaspase 8 cleavage, and accumulation of cleaved caspase 3 and cleaved nuclear PARP products in 24 h, consistent with enhanced TNFR1-mediated apoptosis. Fas/FasL mediated apoptosis was also tested, but no difference was found between Sca-2 positive and negative hepatoma cells.

Intrinsic apoptosis pathway were examined by subjecting the tumor cells to DNA damage signals from UV irradiation or cisplatin treatment. No significant difference in apoptosis was detected between Sca-2 positive and negative hepatoma cells by either of these treatments.

Restoration of the reduced sensitivity to TNFα by lentiviral transduction of a mutant Sca-2 gene. To verify that the phenotype of the lenti Sca-2 siRNA vector transduced tumor cells was indeed caused by Sca-2 suppression rather than alternative siRNA effects, a Sca-2 mutant was designed with three nucleotide changes in the siRNA target site in the Sca-2 coding sequence while maintaining the wild type amino acid sequence. Since siRNA-mediated mRNA degradation is strictly sequence-dependent, Sca-2 expression would be restored in the lenti-siRNA transduced hepatoma cells when the mutant Sca-2 (muSca-2) was introduced into these cells. The muSca-2 gene was cloned into pTYF lentiviral vector (lenti-muSca-2) and the vector was prepared. The Sca-2 siRNA (lenti-Scai-R) transduced hepatoma cells (siSca-2 Td. cells) were infected with lenti-muSca-2 or a control lenti-lacZ virus (lenti-EFnlacZ), and three days later, these transduced cells were analyzed for Sca-2 expression by FACS using anti-Sca-2 antibody. The results demonstrated that lenti-muSca-2, but not lenti-lacZ, effectively restored Sca-2 expression in the siSca-2 Td. cells. The responsiveness of these cell lines to TNF-α was tested. The cells were treated with different concentrations of TNF α for 36 h and stained with Hoechst dye for apoptosis analysis. Results of this assay clearly demonstrated that the tumor cells with reconstituted Sca-2 expression exhibited reduced sensitivity to TNF α-induced apoptosis.

Regulation of TNFR1 Surface Expression by Sca-2.

TNFR1 expression on the tumor cell surface was measured using specific anti-TNFR1 antibody and FACS. Surface TNFR1 expression was analyzed in hepatoma cells transduced with either the lenti-Scai-R (Scai) or a control lentiviral GFP siRNA vector (GFPi) at 3- or 30-days post lentiviral transduction. The results showed that the surface expression of TNFR1 was markedly increased in Scai- but not GFPi-transduced cells. This increase in TNFR1 surface expression occurred rapidly after Sca-2 siRNA inhibition and the expression remained high after 30 days. To see if re-introduction of Sca-2 could affect the surface TNFR1 expression, lenti-muSca-2 or lenti-EFnlacZ was used to infect the 30 DPI Scai transduced hepatoma cells, and the expression of surface TNFR1 was analyzed after 20 days. With rescued Sca-2 expression, the surface TNFR1 expression was down-regulated to levels comparable to the control group. To distinguish between de novo receptor synthesis versus increased surface transport of TNFR1, the total cell lysates were analyzed by Western blotting using anti-TNFR1 antibody. Total TNFR1 was not significantly different between the Sca-2 suppressed (lenti-Scai-R) and the control (lenti-GFPi) hepatoma cells.

Example 2

Lentiviral siRNA Inhibition of HIV-1

Suppression of HV infection by siRNA in acutely and chronically infected host cells was investigated using a self-inactivating lentiviral insulator vector system carrying siRNAs targeting multiple highly conserved HIV-1 sequences. A near 100% inhibition of acute infection was demonstrated using siRNAs targeting highly conserved gag, pol, int and vpu sequences against different strains of HIV-1. These siRNAs also effectively suppressed HIV-1 replication in chronically infected cells and in primary peripheral blood mononuclear cells. The mechanisms of inhibition involve specific viral RNA degradation and silencing of both cytoplasmic and nuclear viral RNAs.

Materials and Methods

Tissue culture and HIV-1 molecular clones. 293T, TE671 and GHOST hi5 cells were cultured in DMEM with 10% FBS, 1% glutamine, and 1% penicillin-streptomycin and propagated to establish more adherent phenotype as previously described. Chang L-J, Zaiss A-K. Methods for the preparation and use of lentivirus vectors. In: Morgan J, ed. Gene Therapy Protocols. Vol. 2. Methods in Molecular Medicine (ed 2nd). Totowa: Humana Press, Inc.; 2001:303-318. The primary peripheral blood mononuclear cells (PBMC) were prepared from healthy donors' buffy coat by density gradient centrifugation using Histopaque (Sigma). GHOST hi5 was derived from HOS cells stably transduced with CD4 and CCR5. CEM-A is a fusion cell clone of CEM and normal PBMC with adherent phenotype susceptible to HIV infection and formation of syncytia. MOLT-3 was purchased from American Type Culture Collection, Rockville, Md. The chronic Molt-3-HIV-1$_{NL4-3}$ producers were generated by infection with low MOI of HIV-1$_{NL4-3}$ and continued propagation until the cells recovered from the cytopathic effects and become long term HIV-1 producers. GHOST hi5, CEM-A and HIV-1 molecular clones p89.6 and p90CF402.1 were obtained through the AIDS Research and Reference Reagent Program, Division of AIDS, NIAID, NIH. The molecular clones of HIV-1$_{NL4-3}$, HIV-1NLAD8 and HIV-2ROD were kindly provided by Dr. M. Martin, Dr. E. Freed (NIH, USA) and Dr. K. Peden (FDA, USA), respectively. The CEM-A and MOLT-3-HIV-1NL4-3 cells were cultured in RPMI 1640 supplemented with 10% fetal bovine serum, 1% glutamine, and 1% penicillin-streptomycin, and the PBMC was cultured in the above RPMI medium supplemented with recombinant human IL-2 (100 u/ml).

Construction of siRNA plasmids and lentiviral transducing vectors. To obtain human H1 promoter, the H1 gene was amplified from the genomic DNA of 293 cells using a 5' primer: (5' to 3') CCATGGAATTCGAACGCTGACGTC (SEQ ID NO:10), and a 3' primer: CCTCACCTCAGCCATTGAACTCAC (SEQ ID NO:11). The H1 promoter was then amplified using the amplified H1 sequence and the same 5' primer and a new 3' primer: -GCAAGCTTAGATCTG TGGTCTCATACAGAACTTATAAGATTCCC- (SEQ ID NO:12), and the amplified DNA was digested with EcoR I and Hind III and cloned into pBSKSII to generate pBS-H1. To facilitate directional cloning, two different Sfi I cloning sites (A and B) were inserted into Xba I and Hind III digested pBS-H1 flanking the H1-promoter region by inserting two linkers with flanking Xba I and Hind III cloning sites using the following four primers: 5'-CTAGAGGCCATTATG-GCCG-3' (SEQ ID NO:13), 5'-AATTCG GCCATAATG-GCCT-3' (SEQ ID NO:14), 5'-AGCTTGGCCGCCTCG-GCC-3' (SEQ ID NO:15), and 5'-TCGAGGCCG AGGCGGCCA-3' (SEQ ID NO:16), to generate pBS-H1-Sfi. The GFP siRNA construct was made by annealing four primers and the HIV-1 siRNA constructs were made by annealing two primers containing the stem-loop siRNA sequence with a 9 nt loop sequence -TTCAAGAGA- (SEQ ID NO:17) and flanking EcoRI and HindIII cloning sites, and then cloned into 3' end of the H1 promoter in the pBS-H1-Sfi plasmid. The siRNA primers used for this study are listed below:

```
GFPi-1:
                                     (SEQ ID NO: 18)
GATCCCCCATTCTCGGCCACAAGCTGTT

GFPi-2:
                                     (SEQ ID NO: 19)
TCTTGAACAGCTTGTGGCCGAGAATGGGG

GFPi-3:
                                     (SEQ ID NO: 20)
CAAGAGACAGCTTGTGGCCGAGAATGTTTTTGGAAA

GFPi-4:
                                     (SEQ ID NO: 21)
AGCTTTTCCAAAAACATTCTCGGCCACAAGCTGTC

U5i-1:
                                     (SEQ ID NO: 22)
GATC CCC GTAGTGTGTGCCCGTCTGT TTCA AGAGA

ACAGACGGGCACACACTAC TTTTT GGAAA

U5i-2:
                                     (SEQ ID NO: 23)
AGCTT TTCC AAAAA GTAGTGTGTGCCCGTCTGT TCT CTT GAA

ACAGACGGGCACACACTAC GGG

1ˢᵗ gagi-1:
                                     (SEQ ID NO: 24)
GATC CCC GAAATGATGACAGCATGTC TTCA AGAGA

GACATGCTGTCATCATTTC TTTTT GGAAA

1ˢᵗ gagi-2:
                                     (SEQ ID NO: 25)
AGCTT TTCC AAAAA GAAATGATGACAGCATGTCTCT CTT GAA

GACATGCTGTCATCATTTC GGG-

2nd gagi-1:
                                     (SEQ ID NO: 26)
GATCCCC TAGTAAGAATGTATAGCCC TTCAAGAGA

GGGCTATACATTCTTACTA TTTTTGGAAA

2ⁿᵈ gagi-2:
                                     (SEQ ID NO: 27)
AGCTTTTCCAAAAA TAGTAAGAATGTATAGCCC TCTCTTGAA

GGGCTATACATTCTTACTA GGG

1ˢᵗ poli-1:
                                     (SEQ ID NO: 28)
GATCCCC GCCAGGAATGGATGGCCCA TTCAAGAGA

TGGGCCATCCATTCCTGGC TTTTTGGAAA

1ˢᵗ poli-2:
                                     (SEQ ID NO: 29)
AGCTTTTCCAAAAA GCCAGGAATGGATGGCCCA TCTCTTGAA

TGGGCCATCCATTCCTGGC GGG
```

-continued

2<sup>nd</sup> poli-1:
(SEQ ID NO: 30)
GATCCCC GGAATTGGAGGAAATGAAC TTCAAGAGA

GTTCATTTCCTCCAATTCC TTTTTGGAAA

2<sup>nd</sup> poli-2:
(SEQ ID NO: 31)
AGCTTTTCCAAAAA GGAATTGGAGGAAATGAAC TCTCTTGAA

GTTCATTTCCTCCAATTCC GGG

1<sup>st</sup> inti-1:
(SEQ ID NO: 32)
GATCCCC TTAGCAGGAAGATGGCCAG TTCAAGAGA

CTGGCCATCTTCCTGCTAA TTTTTGGAAA

1<sup>st</sup> inti-2:
(SEQ ID NO: 33)
AGCTTTTCCAAAAA TTAGCAGGAAGATGGCCAG TCTCTTGAA

CTGGCCATCTTCCTGCTAAGGG

2<sup>nd</sup> inti-1:
(SEQ ID NO: 34)
GATCCCC GGTGAAGGGGCAGTAGTAA TTCAAGAGA

TTACTACTGCCCCTTCACC TTTTTGGAAA

2<sup>nd</sup> inti-2:
(SEQ ID NO: 35)
AGCTTTTCCAAAAAGGTGAAGGGGCAGTAGTAATCTCTTGAA

TTACTACTGCCCCTTCACCGGG

1<sup>st</sup> vpui-1:
(SEQ ID NO: 36)
GATC CCC GACAGTGGCAATGAGAGTGTTCA

AGAGACACTCTCATTGCCACTGTC TTTTT GGAAA

1<sup>st</sup> vpui-2:
(SEQ ID NO: 37)
AGCTT TTCCAAAAAGACAGTGGCAATGAGAGTG TCTCTTGAA

CACTCTCATTGCCACTGTC GGG

2<sup>nd</sup> vpui-1:
(SEQ ID NO: 38)
GATCCCC GAGCAGAAGACAGTGGCAATTCAAGAGA

TTGCCACTGTCTTCTGCTC TTTTTGGAAA

2<sup>nd</sup>-vpui-2:
(SEQ ID NO: 39)
AGCTTTTCCAAAAAGAGCAGAAGACAGTGGCAATCTCTTGAA

TTGCCACTGTCTTCTGCTCGGG nefi-1:-
(SEQ ID NO: 40)
GATC CCC GTAGTGTGATTGGATGGCC TTCA

AGAGAGGCCATCCAATCACACTAC TTTTT GGAAAnefi-2:
(SEQ ID NO: 41)
AGCTT TTCC AAAAGTAGTGTGATTGGATGGCCTCTCTTGAA

GGCCATCCAATCACACTACGGG

U3i-1:
(SEQ ID NO: 42)
GATCCCCGGAGAGAACACCAGCTTGTTTCAAGAGAACAAGCTGGTG

TTCTCTCCTTTTTGGAAA

U3i-2:
(SEQ ID NO: 43)
AGCTT TTCCAAAAAGGAGAGAACACCAGCTTGTTCTCTTGAA

ACAAGCTGGTGTTCTCTCCGGG

A lentiviral SIN-insulator vector (pTYF-EFnlacZcHS) containing two Sfi I (A/B) cloning sites and a 1100 bp stuffer and a chicken HS4 insulator sequence (cHS4) was used to construct all of the lentiviral siRNA vectors. The H1-siRNA fragment was released from the pBS-H1-Sfi-siRNA plasmid by Sfi I digestion and cloned into the reverse lentiviral pTYF-Sfi B/A vector to obtain the siRNA transducing vector. All of the siRNA sequences were confirmed by DNA sequencing.

DNA transfection and HIV-1 preparation. For the analysis of siRNA effect on HIV-1, 293T cells were co-transfected with pBS-H1-Sfi-siRNA (1.8 ug/well) and HIV-1 DNA (0.2 ug/well) in 12-well plates using Superfect as described by the manufacturer (Qiagene). The supernatants were harvested 24 h post-transfection and used for MAGI and (reverse transcriptase) RT assays. For the preparation of HIV-1 stocks, 293T cells were transfected with HIV-1 DNA and the supernatants were collected at 12 h intervals for three times 12 h after DNA addition.

Lentiviral vector preparation, titration and transduction. Lentiviral vectors were generated by DNA co-transfection and the virus was concentrated by microfuge centrifugation or filtration as previously described. Id. The virus titer was determined on TE671 cells using β-galactosidase enzyme assay. For lentiviral transduction, the cells were transduced at different MOI as indicated in the text in the presence of polybrene (8 ug/ml, Sigma). The transduction efficiency was monitored by reporter gene nlacZ assay.

HIV-1 infection, RT and MAGI assays. PBMC was activated with 2 ug/ml phytohemagglutinin (PHA) in RPMI1640 medium for 1 day and the cells were washed three times before lentiviral siRNA vector transduction at 10 MOI. The siRNA transduced PBMCs were challenged with wild type HIV-1 at MOI of 20 after 24 h. At different time points after HIV-1 challenge, the supernatants were harvested for RT assay. At each harvest, the cells were counted and the same number of viable cells was plated with fresh media. The Molt-3 cells were transduced with lentiviral-siRNA vectors in RPMI1640 containing 10 ug/ml polybrene at MOI of 10. To determine virus production, $1 \times 10^5$ cells were seeded into 24-well plate in 300 ul/well of fresh RPMI 1640 and after 24 h, the supernatants were harvested for RT assay.

Cytoplasmic and nuclear RNA analysis. The nuclear and cytoplasmic RNA was harvested as previously described with minor modifications. Zaiss et al., J Virol. 2002; 76:7209-7219. Briefly, the cells were washed 2-3 times with cold PBS, and the cell pellet was resuspended in ice-cold 250 µl solution containing 10 mM Tris pH 7.4, 10 mM NaCl, 3 mM $MgCl_2$ and 25 µl VRC (20 mM, BRL) and gently lysed by adding 12.5 µl 10% NP40, mixed briefly and sitting on ice for 2-3 min. After centrifugation at 800 g for 2 min, the supernatant and the nuclear pellet were separated and the RNA was harvested using TRI reagent (BRL) as described by the manufacturer. The RNA was analyzed by electrophoresis on a formaldehyde agarose gel, blotted and probed with random primed probes (Stratagene, La Jolla, Calif., USA) using sequences specific for full-length HIV-1 or β-actin. For rehybridization, the old probe was stripped by boiling the blots in ddH2O containing 0.1% SDS for 10 min.

Figure 2:
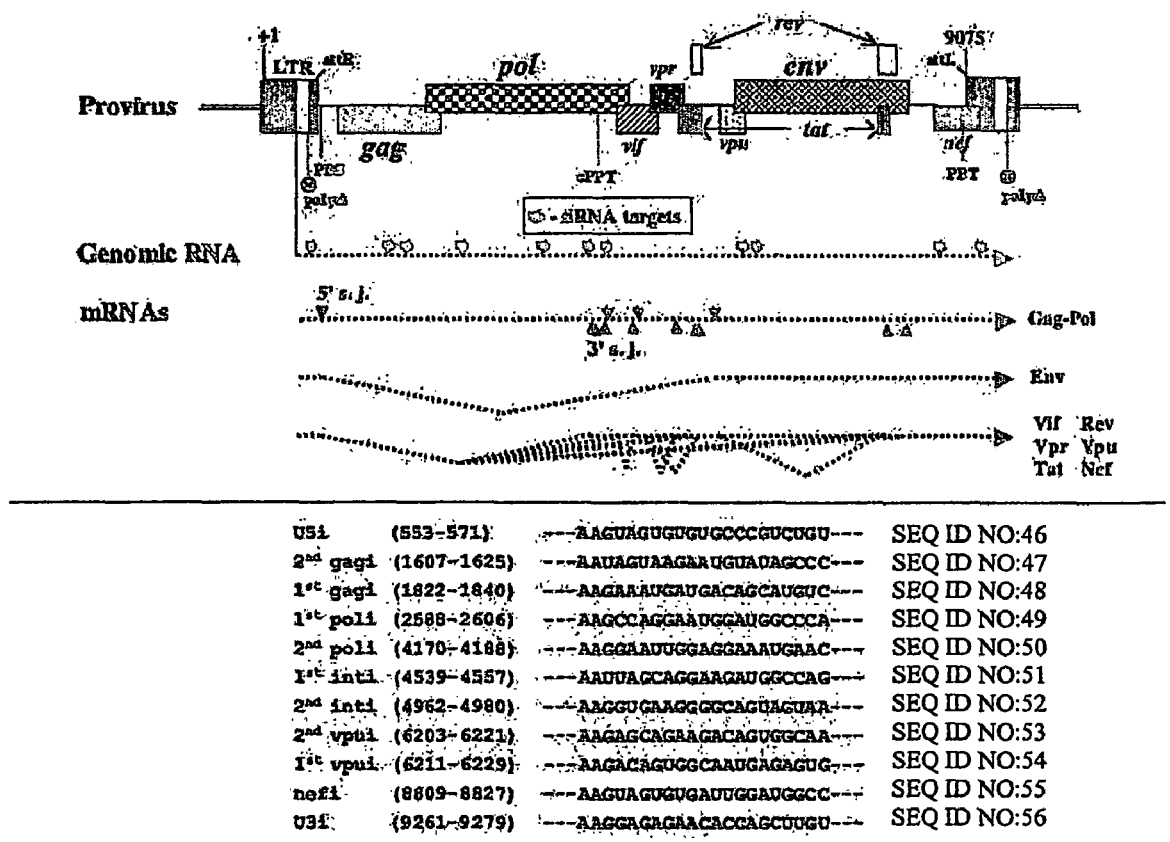
FIG. 2 is schematic illustration of the HIV-1 genome structure, mRNAs and the list of siRNA target sequences. The siRNA target sites are denoted above the dash-lined viral genome with the 5' and 3' splice junction sites marked by arrowheads. The siRNA target sites are shown according to the numerical system of HIV-1$_{NL4-3}$.
Figure 3:
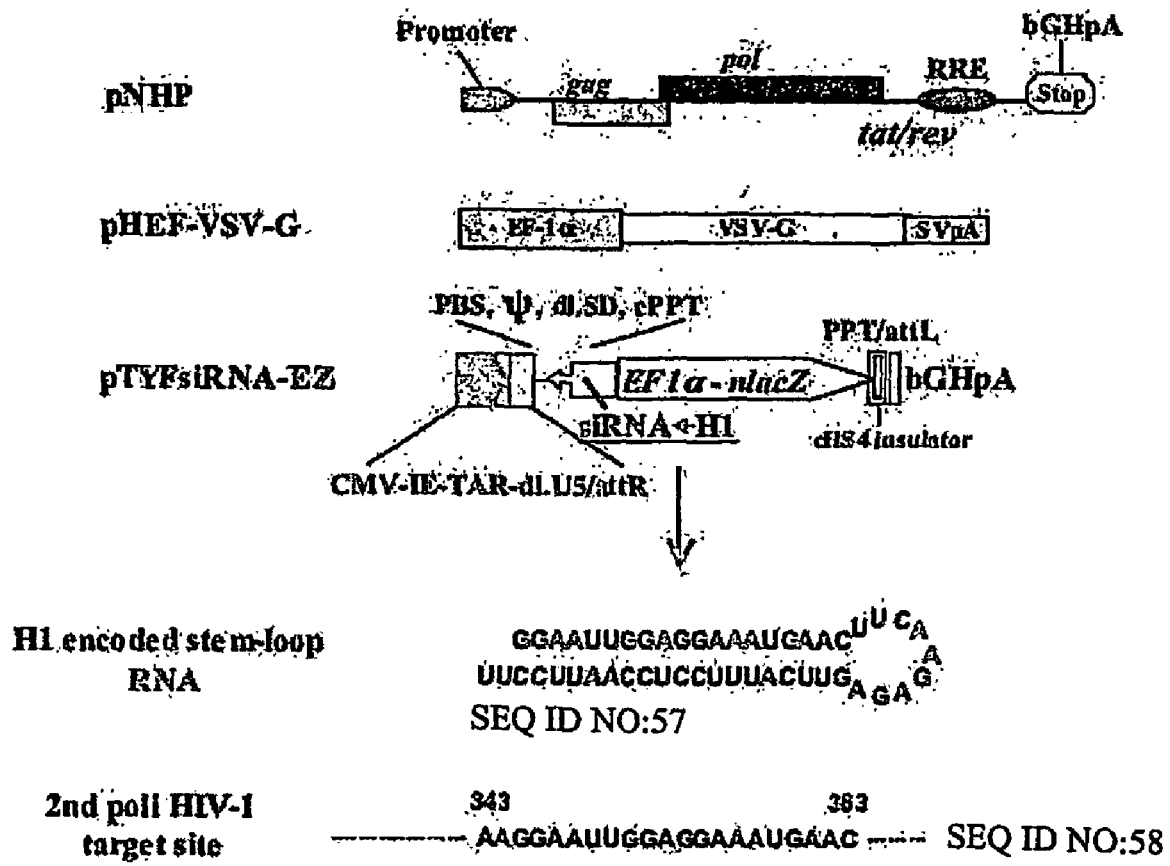
FIG. 3 is schematic illustration of lentiviral vector constructs and predicted siRNA structure. The features of gag-pol and VSV-G expression constructs and the self-inactivating vector are illustrated. The H1 promoter-siRNA cassette is cloned upstream of the EF1α-nlacZ reporter gene. Also illustrated are the predicted stem-loop siRNA precursor and the $2^{nd}$ poli target site.

Results siRNAs targeting multiple highly conserved HIV-1 sequences. To identify multiple siRNA target sites in the HIV-1 genome, the HIV Sequence Compendium was searched. Eleven sites spanning the entire viral genome with highly conserved sequences followed by an AA-di-nucleotide were identified FIG. 2. These sites include non-coding sequences (U5i and U3i) and coding sequences overlapping gag, pol, int, vpu, env ($1^{st}$ vpui) and nef (bottom panel of FIG. 2). The U5i, U3i and nefi target all viral RNA species, while the rest target either full-length or spliced viral RNAs. The siRNA expression vector was constructed by annealing two synthetic oligonucleotides and cloning into a pBS plasmid behind a human H1 polIII promoter. To generate lentiviral siRNA vectors, the H1-siRNA expression cassette was cut out from the pBS-H1 plasmid and ligated into the lentiviral SIN insulator vector in front of an internal EF1α-nlacZ reporter gene as shown in FIG. 3. An example of the predicted 19-nt stem-loop siRNA precursor and its corresponding HIV-1 target sequence ($2^{nd}$ poli) is shown at bottom of FIG. 3.

Efficient inhibition of three HIV-1 strains by siRNAs targeting gag, pol, int and vpu. DNA co-transfection was used to examine the effects of these siRNAs. The pBS siRNA expression plasmid was co-transfected into 293T cells at 20:1 molar ratio with one of the three infectious molecular clones, pNL4-3, p89.6 (p89) and p90CF402.1.8 (p90), and 48 h later, the culture supernatant was collected and assayed for viral RT activity. The siRNA construct (GFPi) targeting the reporter gene GFP was included as control. The RT assay demonstrated that five of the eleven HIV-1-specific siRNA constructs, $1^{st}$ gagi, $2^{nd}$ poli, $2^{nd}$ inti, and both of the vpui, had marked inhibition effect on HIV-$1_{NL4-3}$ and HIV-$1_{89.6}$ (>90%). The HIV-$1_{90CF402.1.8}$, a subtype A/E recombinant, was inhibited by four of the eleven siRNA at >50% efficiencies ($2^{nd}$ gagi, $1^{st}$ poli, $2^{nd}$ inti and $2^{nd}$ vpui). The U5i and U3i siRNAs, which target non-coding regions of the HIV-1 genome, demonstrated ~50% inhibition for HIV-$1_{NL4-3}$ and HIV-$1_{89.6}$, but had no effect on HIV-$1_{90CF402.1.8}$. DNA co-transfection with HIV-2 molecular clone showed no inhibition effect by any of the siRNA constructs.

The RT assay measures HIV Pol protein synthesis and activity. To examine the siRNA effects on viral infectivity, 293T cells were co-transfected with pNL4-3 with these HIV-1 specific siRNA constructs or the gfpi control and 48 h later, the progeny virus was harvested and used to infect CD4+ MAGI cells, an LTR-β-gal reporter cell line. Quantitative comparison of the progeny virus infectivity in MAGI cells after X-gal staining showed that all of the siRNAs targeting viral coding regions were effective in suppressing HIV-1 infection (80-99%) including the nefi construct (~80%) although the latter did not exhibit inhibitory effect by the RT assay. Interestingly, the U5i and U3i, which target non-coding regions in the HIV-1 genome, also exhibited ~50% inhibitory effects.

Protection from HIV-1-induced cytotoxicity after lentiviral siRNA transduction. The transient transfection assay demonstrated that the plasmid siRNA expression constructs were effective in HIV-1 inhibition. Because lentiviral vectors mediate efficient gene delivery and permanent integration into target cells which overcome problems with transient siRNA gene transfer, lentiviral siRNA vectors carrying these HIV-1-specific siRNAs were further tested. Lentiviral siRNA vectors were produced by co-transfection of pNHP, pHEF-VSVG, and pTYFsiRNA-EZ (FIG. 3) into 293T cells and the vector titer was determined on TE671 cells by β-galactosidase reporter gene assay. The titers of these different lentiviral siRNA constructs were compared. All of the lentiviral siRNA constructs produced viral titers in the range of $1-1.5 \times 10^7$/ml. The U5i, gagi, poli, and inti siRNA constructs that also target the helper construct did not significantly affect vector titer. The $2^{nd}$ poli consistently produced lower vector titers than the others, most likely due to efficient siRNA inhibition that also interfered with vector production.

To test lentiviral siRNA inhibition of HIV-1, two human CD4+ cell lines, CEM-A, an adherent lymphoma cell line, and GHOST hi5 cells, both of which are sensitive to M-tropic HIV-1 infection, were first transduced with lentiviral siRNA vectors, gfpi, $2^{nd}$ gagi or $2^{nd}$ vpui. The lentiviral siRNA-transduced CEM-A and GHOST hi5 cells were propagated for 5 days and then challenged with a syncytium-forming HIV-1 (HIV-$1_{NL-AD8}$), and the cells were monitored for syncytium formation. The results showed that the gfpi-transduced CEM-A cells formed syncytia in the entire culture and were mostly killed in six days after viral infection. In contrast, the $2^{nd}$ gagi transduced CEM-A were partially protected and the $2^{nd}$ vpui-transduced CEM-A cells mostly protected from the syncytium-forming cytotoxic effect of HIV-$1_{NL-AD8}$. Similar results were observed in GHOST hi5 cells after lentiviral siRNA transduction and HIV-$1_{NL-AD8}$ challenge. The lentiviral transduction efficiency was close to 100% as indicated by a lacZ reporter gene assay.

Lentiviral siRNA inhibition of HIV-1 in chronically infected human lymphocytes. The transduction and challenge experiments above demonstrated that lentiviral siRNA protected cells from HIV-1 infection and the associated cytopathic effects. Whether lentiviral siRNA could inhibit HIV-1 in established HIV-1-infected cells was investigated. A MOLT-3 human T cell line that has been chronically infected with wild type HIV-1, which continued to produce high titer HIV-1, was transduced with lentiviral siRNA vectors including gfpi, $2^{nd}$ poli, $2^{nd}$ inti, $2^{nd}$ vpui and a combination of all three latter siRNA vectors. The chronically HIV-1-infected MOLT-3 cells have been propagated for longer than 9 months and all cells are infected and produce HIV-1 continuously. After lentiviral siRNA transduction, siRNA transduction was monitored using a lacZ reporter gene assay. Viral RT activity in the culture supernatants was analyzed to determine the siRNA inhibition effects. Lentiviral transduction efficiency of the MOLT-3 cells was >90%, and all three lentiviral siRNA, $2^{nd}$ poli, $2^{nd}$ inti and $2^{nd}$ vpui, but not gfpi, inhibited HIV-1 replication in the chronic HIV-1 positive MOLT-3 cells, and the combination of three different HIV-1-specific siRNA vectors displayed the highest inhibition efficiency (>95%).

To see if the inhibition was due to HIV-1 RNA degradation rather than non-specific viral interference in the MOLT-3 cells, cytoplasmic and nuclear RNAs were harvested and examined. The quality of the RNA was monitored and shown by EtBr staining of the agarose gel. Northern analysis of mock, gfpi and $2^{nd}$ vpui transduced MOLT-3 cells demonstrated marked reduction of all HIV-1 RNA species (full length and spliced RNAs) in the HIV-1 siRNA ($2^{nd}$ vpui) lentivirus-transduced cells, but not in mock- or gfpi-transduced cells. The siRNA inhibition was HIV-1 specific because non-specific RNA degradation was not detected, as shown by the presence of similar amount of β-actin RNA in all of these samples. Lentiviral $2^{nd}$ vpui inhibited HIV-1 RNA in both cytoplasmic (C) and nuclear (N) compartments of the chronically infected MOLT-3 cells.

Lentiviral siRNA inhibition of HIV-1 in primary peripheral blood lymphocytes. To investigate the efficiency of siRNA inhibition of HIV-1 in primary human lymphocytes, primary human PBMCs were transduced with lentiviral siRNA vectors followed by high MOI wild type HIV-1 challenge. A donor's PBMCs were activated with PHA and transduced with lentiviral siRNA vectors encoding gfp $2^{nd}$ poli, or $2^{nd}$ vpui. After lentiviral transduction, the PBMCs were counted and same number of viable cells were plated into 24-well culture dishes and challenged with the primary viral strain HIV-1$_{89.6}$. The efficiency of lentiviral transduction of the PBMCs was estimated at ~15% by β-galactosidase reporter gene assay. The culture supernatants were collected every 1-2 day post-HIV-1 challenge (dpc) for ten days and assayed for RT activity. The RT kinetics showed reduced HIV-1$_{89.6}$ replication in PBMCs that had been transduced with the HIV-1 specific $2^{nd}$ poli and the $2^{nd}$ vpui lentiviral vectors as compared with that of mk and gfpi transduced PBMCs. Similar results were obtained with PBMCs from different donors that were challenged with HIV-1$_{NL4-3}$.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a first lentiviral vector comprising a nucleotide sequence encoding a first small interference RNA, a second lentiviral vector comprising a nucleotide sequence encoding a second small interference RNA, or a third lentiviral vector comprising a nucleotide sequence encoding a third small interference RNA, or a combination of said first, second and third lentiviral vectors, wherein each of the first, second and third small interference RNAs target a different sequence selected from the group consisting of: SEQ ID NO: 49, SEQ ID NO: 51, and SEQ ID NO: 54.

2. The composition of claim 1, wherein the first lentiviral vector is comprised within a viral particle, the second lentiviral vector is comprised within a viral particle, and the third lentiviral vector is comprised within a viral particle.

3. The composition of claim 1, wherein each of the first, second and third lentiviral vectors comprises a cassette comprising a promoter operably linked to the nucleotide sequence encoding the first, second and third small interference RNAs.

4. The composition of claim 3, wherein the cassette is in a reverse orientation relative to the other genetic elements in the first, second and third lentiviral vectors.

5. The composition of claim 3, wherein the cassette is in a forward orientation relative to the other genetic elements in the first, second and third lentiviral vectors.

6. The composition of claim 3, wherein the promoter is in a reverse orientation as compared to the other genetic elements in the first, second and third lentiviral vectors.

7. The composition of claim 3, wherein the promoter is a pol III promoter.

8. The composition of claim 7, wherein the promoter comprises H1 or U6.

9. A composition comprising a lentiviral vector comprising a nucleotide sequence encoding a small interference RNA that targets a sequence selected from SEQ ID NOs: 49, 51, and 54.

* * * * *

SEQUENCE LISTING

<160> NUMBER OF SEQ ID NOS: 58

<210> SEQ ID NO 1
<211> LENGTH: 56
<212> TYPE: DNA
<213> ORGANISM: Artificial
<220> FEATURE:
<223> OTHER INFORMATION: Synthetic Oligonucleotide

<400> SEQUENCE: 1
tttgctcctt ctgcaacttc agttcaagag actgaagttg cagaaggagc tttttt    56

<210> SEQ ID NO 2
<211> LENGTH: 56
<212> TYPE: DNA
<213> ORGANISM: Artificial
<220> FEATURE:
<223> OTHER INFORMATION: Synthetic Oligonucleotide

<400> SEQUENCE: 2
agctaaaaaa gctccttctg caacttcagt ctcttgaact gaagttgcag aaggag    56

<210> SEQ ID NO 3
<211> LENGTH: 55
<212> TYPE: DNA
<213> ORGANISM: Artificial
<220> FEATURE:
<223> OTHER INFORMATION: Synthetic Oligonucleotide

<400> SEQUENCE: 3
tttgagagac cacatggtcc tgttcaagag acaggaccat gtggtctctc ttttt    55

<210> SEQ ID NO 4
<211> LENGTH: 55
<212> TYPE: DNA
<213> ORGANISM: Artificial
<220> FEATURE:
<223> OTHER INFORMATION: Synthetic Oligonucleotide

<400> SEQUENCE: 4
agctaaaaag agagaccaca tggtcctgtc tcttgaacag gaccatgtgg tctct    55

<210> SEQ ID NO 5
<211> LENGTH: 36
<212> TYPE: DNA
<213> ORGANISM: Artificial
<220> FEATURE:
<223> OTHER INFORMATION: Synthetic Oligonucleotide

<400> SEQUENCE: 5
aatctagacc accatgtctg ccacttccaa catgag    36

<210> SEQ ID NO 6
<211> LENGTH: 49
<212> TYPE: DNA
<213> ORGANISM: Artificial
<220> FEATURE:
<223> OTHER INFORMATION: Synthetic Oligonucleotide

<400> SEQUENCE: 6
gtgaacagct actgctgcca atcgtcgttc tgcaacttca gcgcagctg                49

<210> SEQ ID NO 7
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 7
aagaattctg gtcaggggct cagctgcag                                      29

<210> SEQ ID NO 8
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 8
gctccttctg caacttcagt t                                              21

<210> SEQ ID NO 9
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 9
ctgaagttgc agaaggagct t                                              21

<210> SEQ ID NO 10
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 10
ccatggaatt cgaacgctga cgtc                                           24

<210> SEQ ID NO 11
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 11
cctcacctca gccattgaac tcac                                           24

<210> SEQ ID NO 12
<211> LENGTH: 44
<212> TYPE: DNA
<213> ORGANISM: Artificial
<220> FEATURE:

<223> OTHER INFORMATION: Synthetic Oligonucleotide

<400> SEQUENCE: 12
gcaagcttag atctgtggtc tcatacagaa cttataagat tccc     44

<210> SEQ ID NO 13
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 13
ctagaggcca ttatggccg     19

<210> SEQ ID NO 14
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 14
aattcggcca taatggcct     19

<210> SEQ ID NO 15
<211> LENGTH: 18
<212> TYPE: DNA
<213> ORGANISM: Artificial
<220> FEATURE:
<223> OTHER INFORMATION: Synthetic Oligonucleotide

<400> SEQUENCE: 15
agcttggccg cctcggcc     18

<210> SEQ ID NO 16
<211> LENGTH: 18
<212> TYPE: DNA
<213> ORGANISM: Artificial
<220> FEATURE:
<223> OTHER INFORMATION: Synthetic Oligonucleotide

<400> SEQUENCE: 16
tcgaggccga ggcggcca     18

<210> SEQ ID NO 17
<211> LENGTH: 9
<212> TYPE: DNA
<213> ORGANISM: Artificial
<220> FEATURE:
<223> OTHER INFORMATION: Synthetic Oligonucleotide

<400> SEQUENCE: 17 ttcaagaga     9

<210> SEQ ID NO 18
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 18
gatcccccat tctcggccac aagctgtt     28

<210> SEQ ID NO 19
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 19
tcttgaacag cttgtggccg agaatgggg                               29

<210> SEQ ID NO 20
<211> LENGTH: 36
<212> TYPE: DNA
<213> ORGANISM: Artificial
<220> FEATURE:
<223> OTHER INFORMATION: Synthetic Oligonucleotide

<400> SEQUENCE: 20
caagagacag cttgtggccg agaatgtttt tggaaa                       36

<210> SEQ ID NO 21
<211> LENGTH: 35
<212> TYPE: DNA
<213> ORGANISM: Artificial
<220> FEATURE:
<223> OTHER INFORMATION: Synthetic Oligonucleotide

<400> SEQUENCE: 21
agcttttcca aaacattct cggccacaag ctgtc                         35

<210> SEQ ID NO 22
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 22
gatccccgta gtgtgtgccc gtctgtttca agagaacaga cgggcacaca ctacttttg    60 gaaa                                                               64

<210> SEQ ID NO 23
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 23
agcttttcca aaagtagtg tgtgcccgtc tgttctcttg aaacagacgg gcacacacta    60
cggg                                                               64

<210> SEQ ID NO 24
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 24
gatccccgaa atgatgacag catgtcttca agagagacat gctgtcatca tttcttttg    60 gaaa                                                               64

<210> SEQ ID NO 25

```
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 25
agcttttcca aaagaaatg atgacagcat gtctctcttg aagacatgct gtcatcattt    60
cggg                                                                64

<210> SEQ ID NO 26
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 26
gatcccctag taagaatgta tagcccttca agagagggct atacattctt actatttttg    60
gaaa                                                                64

<210> SEQ ID NO 27
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 27
agcttttcca aaatagtaa gaatgtatag ccctctcttg aagggctata cattcttact    60
aggg                                                                64

<210> SEQ ID NO 28
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 28
gatccccgcc aggaatggat ggcccattca agagatgggc catccattcc tggcttttg    60 gaaa                                                                64

<210> SEQ ID NO 29
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 29
agcttttcca aaagccagg aatggatggc ccatctcttg aatgggccat ccattcctgg    60
cggg                                                                64

<210> SEQ ID NO 30
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 30
gatccccgga attggaggaa atgaacttca agagagttca tttcctccaa ttccttttg    60
``` gaaa                                                                64

<210> SEQ ID NO 31
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 31
agcttttcca aaaaggaatt ggaggaaatg aactctcttg aagttcattt cctccaattc    60
cggg                                                                64

<210> SEQ ID NO 32
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 32
gatcccctta gcaggaagat ggccagttca agagactggc catcttcctg ctaattttg     60 gaaa                                                                64

<210> SEQ ID NO 33
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 33
agcttttcca aaaattagca ggaagatggc cagtctcttg aactggccat cttcctgcta    60
aggg                                                                64

<210> SEQ ID NO 34
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 34
gatccccggt gaaggggcag tagtaattca agagattact actgcccctt cacttttttg   60
gaaa                                                                64

<210> SEQ ID NO 35
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 35
agcttttcca aaaaggtgaa ggggcagtag taatctcttg aattactact gccccttcac    60
cggg                                                                64

<210> SEQ ID NO 36
<211> LENGTH: 64
<212> TYPE: DNA
<213> ORGANISM: Artificial
<220> FEATURE:

-continued

```
<223> OTHER INFORMATION: Synthetic Oligonucleotide

<400> SEQUENCE: 36
gatccccgac agtggcaatg agagtgttca agagacactc tcattgccac tgtcttttg    60 gaaa                                                                 64

<210> SEQ ID NO 37
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 37
agcttttcca aaagacagt ggcaatgaga gtgtctcttg aacactctca ttgccactgt    60
cggg                                                                 64

<210> SEQ ID NO 38
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 38
gatccccgag cagaagacag tggcaattca agagattgcc actgtcttct gctcttttg    60 gaaa                                                                 64

<210> SEQ ID NO 39
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 39
agcttttcca aaagagcag aagacagtgg caatctcttg aattgccact gtcttctgct    60
cggg                                                                 64

<210> SEQ ID NO 40
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 40
gatccccgta gtgtgattgg atggccttca agagaggcca tccaatcaca ctactttttg    60
gaaa                                                                 64

<210> SEQ ID NO 41
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 41
agcttttcca aaagtagtg tgattggatg gcctctcttg aaggccatcc aatcacacta    60
cggg                                                                 64
```

```
<210> SEQ ID NO 42
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 42
gatccccgga gagaacacca gcttgtttca agagaacaag ctggtgttct ctccttttg      60 gaaa                                                                   64

<210> SEQ ID NO 43
<211> LENGTH: 64
<212> TYPE: DNA
<213> ORGANISM: Artificial
<220> FEATURE:
<223> OTHER INFORMATION: Synthetic Oligonucleotide

<400> SEQUENCE: 43
agcttttcca aaaggagag aacaccagct tgttctcttg aaacaagctg gtgttctctc       60
cggg                                                                   64

<210> SEQ ID NO 44
<211> LENGTH: 21
<212> TYPE: RNA
<213> ORGANISM: Mus musculus

<400> SEQUENCE: 44
aagcuccuuc ugcaacuuca g                                                21

<210> SEQ ID NO 45
<211> LENGTH: 49
<212> TYPE: RNA
<213> ORGANISM: Mus musculus

<400> SEQUENCE: 45
gcuccuucug caacuucagu ucaagagacu gaaguugcag aaggagcuu                  49

<210> SEQ ID NO 46
<211> LENGTH: 21
<212> TYPE: RNA
<213> ORGANISM: Human immunodeficiency virus type 1

<400> SEQUENCE: 46
aaguagugug ugcccgucug u                                                21

<210> SEQ ID NO 47
<211> LENGTH: 21
<212> TYPE: RNA
<213> ORGANISM: Human immunodeficiency virus type 1

<400> SEQUENCE: 47
aauaguaaga auguauagcc c                                                21

<210> SEQ ID NO 48
<211> LENGTH: 21
<212> TYPE: RNA
<213> ORGANISM: Human immunodeficiency virus type 1

<400> SEQUENCE: 48
aagaaaugau gacagcaugu c                                                21

<210> SEQ ID NO 49
```

```
<211> LENGTH: 21
<212> TYPE: RNA
<213> ORGANISM: Human immunodeficiency virus type 1

<400> SEQUENCE: 49
aagccaggaa uggauggccc a                                          21

<210> SEQ ID NO 50
<211> LENGTH: 21
<212> TYPE: RNA
<213> ORGANISM: Human immunodeficiency virus type 1

<400> SEQUENCE: 50
aaggaauugg aggaaaugaa c                                          21

<210> SEQ ID NO 51
<211> LENGTH: 21
<212> TYPE: RNA
<213> ORGANISM: Human immunodeficiency virus type 1

<400> SEQUENCE: 51
aauuagcagg aagauggcca g                                          21

<210> SEQ ID NO 52
<211> LENGTH: 21
<212> TYPE: RNA
<213> ORGANISM: Human immunodeficiency virus type 1

<400> SEQUENCE: 52
aaggugaagg ggcaguagua a                                          21

<210> SEQ ID NO 53
<211> LENGTH: 21
<212> TYPE: RNA
<213> ORGANISM: Human immunodeficiency virus type 1

<400> SEQUENCE: 53
aagagcagaa gacaguggca a                                          21

<210> SEQ ID NO 54
<211> LENGTH: 21
<212> TYPE: RNA
<213> ORGANISM: Human immunodeficiency virus type 1

<400> SEQUENCE: 54
aagacagugg caaugagagu g                                          21

<210> SEQ ID NO 55
<211> LENGTH: 21
<212> TYPE: RNA
<213> ORGANISM: Human immunodeficiency virus type 1

<400> SEQUENCE: 55
aaguagugug auuggauggc c                                          21

<210> SEQ ID NO 56
<211> LENGTH: 21
<212> TYPE: RNA
<213> ORGANISM: Human immunodeficiency virus type 1

<400> SEQUENCE: 56
aaggagagaa caccagcuug u                                          21
```

-continued

```
<210> SEQ ID NO 57
<211> LENGTH: 49
<212> TYPE: RNA
<213> ORGANISM: Homo sapiens

<400> SEQUENCE: 57
ggaauuggag gaaaugaacu ucaagagagu ucauuccuc caauuccuu            49

<210> SEQ ID NO 58
<211> LENGTH: 21
<212> TYPE: RNA
<213> ORGANISM: Human immunodeficiency virus type 1

<400> SEQUENCE: 58
aaggaauugg aggaaaugaa c                                         21
```